United States Patent

Steinmeyer et al.

[11] Patent Number: 5,886,233
[45] Date of Patent: Mar. 23, 1999

[54] CYCLOHEXANONE DERIVATIVES, PROCESS FOR THEIR PRODUCTION AND INTERMEDIATE PRODUCTS OF THE PROCESS

[75] Inventors: Andreas Steinmeyer, Berlin; Gunter Neef, Berlin; Gunnar Muller, Berlin; Hans-Joachim Knölker, Leopoldshafen, all of Germany

[73] Assignee: Schering Aktiengesellschaft, Germany

[21] Appl. No.: 765,102

[22] PCT Filed: Jun. 13, 1995

[86] PCT No.: PCT/EP95/02274

§ 371 Date: Aug. 8, 1997

§ 102(e) Date: Aug. 8, 1997

[87] PCT Pub. No.: WO96/00207

PCT Pub. Date: Jan. 4, 1996

[30] Foreign Application Priority Data

Jun. 23, 1994 [DE] Germany .......... 44 23 669.7

[51] Int. Cl.[6] .................................. C07C 49/29

[52] U.S. Cl. .................. 568/376; 568/388; 568/389; 549/381; 549/429; 556/466

[58] Field of Search .................. 568/376, 388, 568/389, 391; 549/381, 429; 556/466

[56] References Cited

PUBLICATIONS

Maruoka et al., "Unusual Conjugate Addition of Organolithium Reagent to α,β–Unsaturated Ketone," Tetrahedron Letters, vol. 28, No. 46, pp. 5723–5726, 1987.

Maruoka et al., "Amphiphilic Reactions by Means of Exceptionally Bulky Organoaluminum Reagents," J. Am. Chem. Soc., 110, pp. 3588–3597, 1988.

The Journal of Organic Chemistry, vol. 54, No. 15, pp. 3514–3519, 1989.

Castedo et al., An Improved Synthesis of 1α, 25–Dihydroxyvitamin D A Synthons[1], Tetrahedron Letters, vol. 28, No. 19, pp. 2099–2102, 1987.

*Primary Examiner*—Shailendra Kumar
*Assistant Examiner*—Sreeni Padmanabhan
*Attorney, Agent, or Firm*—Miller, White, Zelano & Branigan, P.C.

[57] ABSTRACT

Described are cyclohexanone derivatives of the formula (I), a method of preparing them and intermediates used in their preparation.

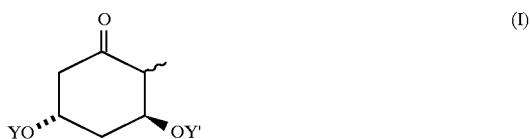

(I)

12 Claims, No Drawings

CYCLOHEXANONE DERIVATIVES, PROCESS FOR THEIR PRODUCTION AND INTERMEDIATE PRODUCTS OF THE PROCESS

This is the U.S. National stage Application of PCT/EP95/02279, filed Jun. 13, 1995 now WO 96/00207 published Jan. 4, 1996.

The following invention relates to cyclohexanone derivatives of general formula I,

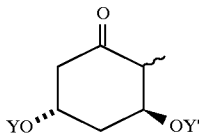
(I)

in which Y and Y' can be the same or different. Specifically, Y and Y' can each mean a hydrogen atom, an alkanoyl group with 1 to 9 carbon atoms or an aroyl group or an alkyl-substituted or aryl-substituted or mixed aryl-alkyl-substituted silyl group or another standard hydroxyl protective group (see T. W. Greene and P. G. M. Wuts, Protective Groups in Organic Synthesis (2nd Ed.), pp. 10–118, Wiley, 1991).

Y and Y' preferably mean the acetyl, propionyl, pivaloyl or benzoyl group or the trimethylsilyl (TMS), triethylsilyl (TES), tert-butyldimethylsilyl (TBDMS), tert-butyldiphenylsilyl (TBDPS) or triisopropylsilyl protective group (TIPS) or the methoxymethyl (MOM), methoxyethoxymethyl (MEM), ethoxyethyl (EE), trimethylsilylethoxymethyl (SEM), tetrahydrofuranyl (THF) or tetrahydropyranyl group (THP).

This invention further relates to a process for the production of the cyclohexanone derivatives of general formula I and intermediate products for synthesis of vitamin D-A-ring fragments and 1α-hydroxy vitamin D derivatives.

Especially preferred are the following cyclohexanone derivatives:
(3S,5S)-3,5-Bis[[dimethyl(1,1-dimethylethyl)silyl]oxy]-2-methylcyclohexanone
(3S,5S)-3,5-bis[[(1,1-dimethylethyl)-diphenylsilyl]oxy]-2-methylcyclohexanone
(3S,5S)-3,5-bis[(triethylsilyl)oxy]-2-methylcyclohexanone
(3S,5S)-3,5-bis(acetyloxy)-2-methylcyclohexanone
(3S,5S)-3,5-bis(2,2-dimethyl-1-oxopropoxy)-2-methylcyclohexanone
(3S,5S)-3,5-bis(benzoyloxy)-2-methylcyclohexanone
(3S,5S)-3,5-bis(1-ethoxyethoxy)-2-methylcyclohexanone.

In addition, the following intermediate products of synthesis as well as the process for their production are claimed,

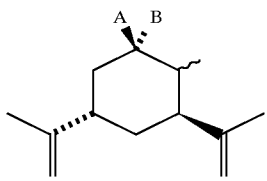
IX

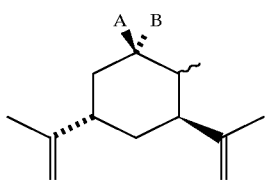
X

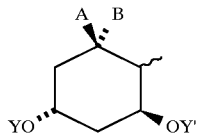
XII in which A and B together mean a free or protected carbonyl group (protective groups: dialkoxyketal, 1,3-dioxane, 1,3-dioxolane, dialkylhydrazone, tosylhydrazone, oxime, alkyl- or benzyloxime ether, or A or B means a hydrogen atom and the corresponding other group B or A means a hydroxy group, which can be free or protected (protective groups: benzyl ether, p-methoxybenzyl ether, o-, m-, p-nitrobenzyl ether, TBDMS ether, TIPS ether, TBDPS ether, TES ether, MOM ether, MEM ether, SEM ether, EE ether, THP ether, THF ether or the like). The meanings for Y and Y' correspond to the groups that are indicated for general formula I.

Especially preferred are the following intermediate products:
(1S,5S)-1,5-Bis(1-methylethenyl)-2-methyl-3-(phenylmethoxy)cyclohexane
(1S,3S)-1,1'-[4-methyl-5-(phenylmethoxy)-1,3-cyclohexanediyl]bis[ethanone]
(1S,5R)-1,5-bis(acetyloxy)-2-methyl-3-(phenylmethoxy)-cyclohexane
(1S,3S)-4-methyl-5-(phenylmethoxy)-1,3-cyclohexanediol
(1S,5R)-1,5-bis[[dimethyl(1,1-dimethylethyl)silyl]oxy]-2-methyl-3-(phenylmethoxy)cyclohexane
(3S,5R)-3,5-bis[[dimethyl(1,1-dimethylethyl)silyl]oxy]-2-methylcyclohexanol
(3S,5R)-3,5-bis(acetyloxy)-2-methylcyclohexanol
(E)-(3S,5S)-3,5-bis(1-methylethenyl)-2-methylcyclohexanone oxime
(Z)-(3S,5S)-3,5-bis(1-methylethenyl)-2-methylcyclohexanone oxime
(E)-(3S,5S)-3,5-bis(1-methylethenyl)-2-methylcyclohexanone-O-methyloxime
(Z)-(3S,5S)-3,5-bis(1-methylethenyl)-2-methylcyclohexanone-O-methyloxime
(E)-(1S,3S)-1,1'-[5-(hydroxyimino)-4-methyl-1,3-cyclohexanediyl]bis[ethanone]
(Z)-(1S,3S)-1,1'-[5-(hydroxyimino)-4-methyl-1,3-cyclohexanediyl]bis[ethanone]
(E)-(1S,3S)-1,1'-[5-(methoxyimino)-4-methyl-1,3-cyclohexanediyl]bis[ethanone]
(Z)-(1S,3S)-1,1'-[5-(methoxyimino)-4-methyl-1,3-cyclohexanediyl]bis[ethanone]
(E)-(3S,5R)-3,5-bis(acetyloxy)-2-methylcyclohexanone oxime
(E)-(3S,5R)-3,5-bis(acetyloxy)-2-methylcyclohexanone-O-methyloxime
(Z)-(3S,5R)-3,5-bis(acetyloxy)-2-methylcyclohexanone-O-methyloxime
(E)-(3S,5R)-3,5-dihydroxy-2-methylcyclohexanone oxime
(Z)-(3S,5R)-3,5-dihydroxy-2-methylcyclohexanone oxime
(E)-(3S,5R)-3,5-dihydroxy-2-methylcyclohexanone-O-methyloxime
(Z)-(3S,5R)-3,5-dihydroxy-2-methylcyclohexanone-O-methyloxime
(E)-(3S,5R)-3,5-bis[[dimethyl(1,1-dimethylethyl)silyl]oxy]-2-methylcyclohexanone oxime
(Z)-(3S,5R)-3,5-bis[[(dimethyl(1,1-dimethylethyl)silyl]oxy]-2-methylcyclohexanone oxime
(E)-(3S,5R)-3,5-bis[[dimethyl(1,1-dimethylethyl)silyl]oxy]-2-methylcyclohexanone-O-methyloxime
(Z)-(3S,5R)-3,5-bis[[(dimethyl(1,1-dimethylethyl)silyl]oxy]-2-methylcyclohexanone-O-methyloxime (1S,5S)-1,5-bis(1-methylethenyl)-3-[[(1,1-dimethylethyl) diphenylsilyl]oxy]-2-methylcyclohexane
(1S,3S)-1,1'-[5-[[(1,1-dimethylethyl)diphenylsilyl]oxy]-4-methyl-1,3-cyclohexanediyl]bis[ethanone]
(1S,5S)-1,5-bis(acetyloxy)-3-[[(1,1-dimethylethyl) diphenylsilyl]oxy]-2-methylcyclohexane
(1S,3S)-5-[[(1,1-dimethylethyl)diphenylsilyl]oxy]-4-methyl-1,3-cyclohexanediol
(1S,5S)-1,5-bis(1-ethoxyethoxy)-3-[[(1,1-dimethylethyl) diphenylsilyl]oxy]-2-methylcyclohexane
(3S,5R)-3,5-bis(1-ethoxyethoxy)-2-methylcyclohexanol The advantage of this invention lies in the fact that starting from carvone, an A-ring fragment is created, which right in the first step contains identical substitution patterns in the 3- and 5-positions, and all subsequent synthetic manipulations at these sites can proceed simultaneously. Within the prior art, already similar syntheses, also starting from carvone, are described, in which the sites are synthesized in the 3- and 5-positions with the aid of a prolonged, complex synthesis method to obtain a trans-diol structure [Tetrahedron Letters, Vol. 28, 2099–2102 (1987) and J. Org. Chem. 54, 3515–3517 (1989)].

All compounds of general formulas I, IX, X and XII can be produced from the corresponding precursors by standard reactions, cf. reaction diagrams 1 and 2.

Derivatives of general formula I can be converted readily to 1α-hydroxy-vitamin D-A-ring fragments of general formula II,

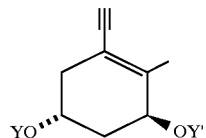

II in which Y and Y' have the already described meaning. Type II compounds are known in the literature and can be converted with suitable CD ring fragments and established sequence chemistry, as is generally known, to 1α-hydroxy-vitamin D analogs [B. Lythgoe et al. Tetrahedron Lett. 3649 (1973), J. Chem. Soc. Perk. I 2654 (1974), A. Mourino et al. Tetrahedron Lett. 29, 1203 (1988), W. H. Okamura et al. J. Org. Chem. 54, 4072 (1989) and EP 0 521 550 A2].

In this case, primarily type III eninene derivatives are produced,

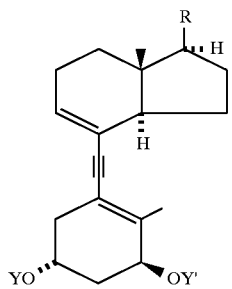

III from which 1α-hydroxy-vitamin D derivatives of general formula IV can be produced by Lindlar hydrogenation of the triple bond into the cis-double bond and subsequent thermally induced 1,7-hydrogen displacement. In this case, radical R means one of the natural vitamin D side chains or one of the artificial vitamin D side chains known in the literature.

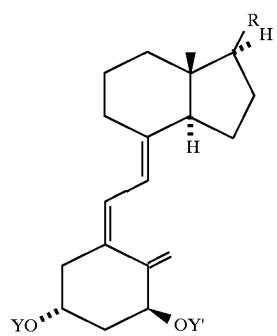

IV

This invention thus represents a new process for the synthesis of intermediate products for the production of 1α-hydroxy-vitamin D analogs.

The latter can be used in the selection of suitable side chains for the production of pharmaceutical agents for treating specific diseases (psoriasis, malignant tumors, acne, auto-immune diseases, wound healing, osteoporosis, etc.). Examples of corresponding derivatives, their biological actions and the target indications are documented in the following patent applications:

Schering AG EP 421 561, WO 91/12238, DE 40 03 854, DE 41 01 953, DE 41 41 746, WO 93/12081, DE 42 20 757, WO 94/00428, DE 42 21 961 WO 94/00429, DE 42 34 382, DE 43 17 415, WO 94/07853.

The conversion of I into II can be accomplished by reaction with lithium, sodium or potassium acetylide or the corresponding mono-trimethylsilylacetylide to a compound of general formula V

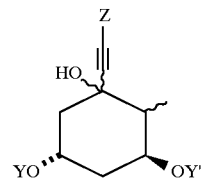

V whereby Z means a hydrogen atom or the trimethylsilyl group. II is obtained by subsequent water elimination (e.g., POCl, pyridine; SOCl$_2$, pyridine; heating with anhydrous copper sulfate, Burgess reagent; action of diethylamino sulfur trifluoride; action of acid, such as mineral acids, acetic acid, oxalic acid, trifluoroacetic acid) or conversion of the hydroxyl group to a leaving group with subsequent elimination (e.g., mesylate or tosylate and base action; xanthogenate or acetate and pyrolysis) followed by possible separation of the regioisomers.

Another strategy comprises the reaction of I to a thermodynamically controlled enol derivative of general formula VI (e.g., enol triflate X=OSO$_2$CF$_3$; enol nonaflate X=OSO$_2$C$_4$F$_9$; vinyl halide X=F, Cl, Br, I) and coupling with a suitable acetylene (e.g., trimethylsilyl acetylene) or the reaction of the corresponding vinyl stannanes (X=alkyl$_3$Sn) or vinyl boric acids or their esters (X=B(OH)$_2$, B(OR)$_2$) with haloacetylene in palladium-catalyzed reactions to II [K. Ritter Synthesis 735 (1993), S. Cacchi Synthesis 320 (1986), L. Brandsma Synth. Comm. 20, 1889 (1990), N. Miyaura et al. Tetrahedron Lett. 22, 127 (1981)]. Here, the possibility also arises of directly coupling said enol derivative VI, whereby X=OSO$_2$CF$_3$; X=OSO$_2$C$_4$F$_9$; X=F, Cl, Br, I; with a suitably substituted vitamin D-CD fragment [e.g., VII, W. H. Okamura et al., J. Org. Chem. 49, 2152 (1984)].

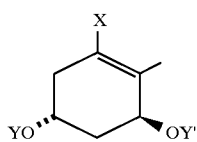

VI

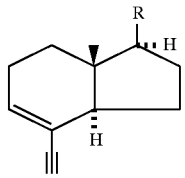

VII

The synthesis of the compounds of general formula I according to the invention is carried out in a new, very direct method that starts from (S)-carvone (commercially available), which is converted in a conjugated addition with a suitable organometallic compound (isopropenyl-cuprate, isopropenyl magnesium halides under copper catalysis) to compound VIII.

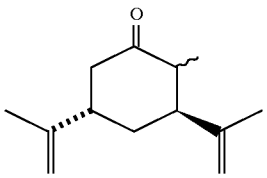

VIII

The introduction of the isopropenyl group is carried out quite selectively from the β-side of the molecule, whereby the absolute and relative configuration that is required for the calcitriol derivative is built up in the subsequent 1- and 3-positions. An advantage of this approach, moreover, is the similar substitution of these sites, so that all chemical manipulations can be performed simultaneously.

The keto group in VIII is now protected under standard conditions as ketal, hydrazone or the like or is reduced to alcohol with a reducing agent (e.g., NaBH$_4$, LiAlH$_4$, DIBAH, Super-Hydride, Selectride, Meerwein-Ponndorf conditions, boranes), which is then provided with a protective group, which must tolerate the subsequent reaction conditions (e.g., benzyl ether, even aryl-substituted; TBDPS ether; TBDMS ether, etc.), whereby derivatives of general formula IX are produced,

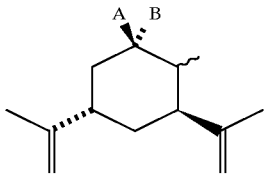

IX in which A and B have the meanings already described above.

Below, the two vinyl groups are degraded to form the corresponding methyl ketones of general formula X.

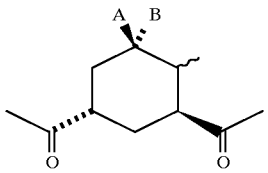

X

For this reaction, an ozonolysis with mild reductive working-up (triphenylphosphine, dimethylsulfide, amines) is suitable. The dihydroxylation of the double bonds under standard conditions (e.g., KMnO$_4$; OSO$_4$, reoxidizing agent) followed by glycol cleavage (e.g., NaIO$_4$; HIO$_4$; Pb(OAc)$_4$) is also possible. In a double Baeyer-Villiger reaction, X is then converted to diacetate XI.

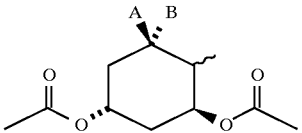

XI

A survey on the considerable number of applicable methods provides a review article: G. R. Krow Org. React. 43, 251 (1993). To be emphasized is a novel method that does not require the use of highly concentrated oxidizing agents such as 90% hydrogen peroxide or 100% MCPBA: urea/H$_2$O$_2$ adduct, trifluoroacetic anhydride [M. S. Cooper, H. Heaney, A. J. Newbold, W. R. Sanderson Synlett 533 (1990)]. This method appears especially suitable for industrial use and actually provides the best results in the case indicated here. Then, the acetates can cleave to form the free hydroxy groups and other protective groups are introduced (e.g., TBDMS, EE), whereby the compound of general formula XII is obtained. The acetates can also be retained, however.

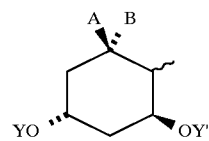

XII

The definitions of A, B and Y as well as Y' were already given earlier.

If A and B mean a carbonyl protective group, the cleavage of this group (e.g., ketal: acid catalysis; oxime alkyl ether: TiCl$_3$, DIBAH or sodium bisulfite; oximebenzyl ether: hydrogenolysis) results directly in the compound of general formula I, while for A=hydrogen and B=hydroxy protective group or vice versa, the corresponding cleavage (silyl groups; TBAF, HF or HF/pyridine; benzyl ether: hydrogenolysis) yields the compound of general formula XIII.

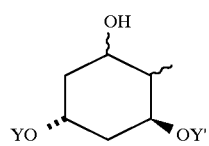

XIII

The reaction to I is then carried out by oxidation with a suitable oxidizing agent, e.g., RuO$_2$/NaIO$_4$[K. Sakai Tetrahedron Asymmetry 3, 297 (1992)] or Swern conditions. As an alternative, other oxidation methods are also conceivable: e.g., PCC, PDC, Dess-Martin reagent, BaMnO$_4$.

By the described new process and taking commercially available (S)-carvone as a starting material, a type II 1α-hydroxy-vitamin D-A-ring fragment is produced, whereby all chemical manipulations can be implemented very easily and can be readily scaled up to production levels.

The total yield of the sequence, without expensive optimizing tests, lies between 16 and 18% over 11 stages. This process thus offers considerable advantages compared to the syntheses of II or corresponding precursor derivatives that are described in the literature [A. Mourino et al. Tetrahedron Lett. 28, 2099 (1987), M. R. Uskokovic et al. Tetrahedron Lett. 28, 2095 (1987), S. Takano et al. J. Org. Chem. 54, 3515 (1989)]. These processes are of academic interest at best due in part to poor yields as well as the use of more expensive reaction conditions or expensive, harmful reagents.

The following examples are used to explain the invention.

EXAMPLES

(3S,5S)-3,5-Bis(1-methylethenyl)-2-methylcyclohexanone 1

95 ml of a 1.7M tert-butyllithium solution in pentane (160 mmol) is slowly added in drops to a solution of 9.68 g (80 mmol) of 2-bromo-1-propene in 160 ml of absolute diethyl ether at −78° C., and it is stirred for 1 more hour at the given temperature. Then, 3.58 g (40 mmol) of copper(I) cyanide is added, and the reaction mixture is slowly heated to −20° C. and kept for 30 minutes at this temperature. Ultimately, the reaction mixture is again cooled to −78° C. and mixed with 4.51 g (30 mmol) of (S)-carvone.

Then, the reaction mixture is slowly heated to room temperature and carefully quenched with saturated ammonium chloride solution. After dilution with ethyl acetate, it is washed another three times with saturated ammonium chloride solution, and the combined aqueous phases are re-extracted another two times with ethyl acetate. The combined organic phases are washed with saturated sodium chloride solution, dried on sodium sulfate, filtered, and the solvent is drawn off in a rotary evaporator. The residue is purified on a silica gel column (mobile solvent: EE:H=1:9, $R_f$=0.8).

5.48 g (28.47 mmol) of title compound 1 is obtained as a colorless liquid.

In general, the spectroscopic data of the main diastereomer are indicated.

$^1$H-NMR (300 MHz, CDCl$_3$): δ=s 4.95 ppm (1H); s 4.80 ppm (1H); s 4.75 ppm (1H); s 4.525 ppm (1H); m 2.75–2.55 ppm (3H); dd 2.525 ppm [5+1]Hz (1H); ddd 2.30 ppm [15+10+1]Hz (1H); m 2.00 ppm (1H); dd 1.825 [10+5](1H); s 1.725 ppm (3H); s 1.70 ppm (3H); d 1.075 ppm [7.5](3H)

MS (EI): m/z=192 (M$^+$) [3%]; 177 (M$^+$) [2%]; 95 [32%]; 83 [100%]

IR (CHCl$_3$): ν=1701, 1451, 1377, 901 cm$^{-1}$

Production of 1 by Grignard Reaction 5.4 g (220 mmol) of magnesium chips in 60 ml of THF is introduced, and 25.41 g (210 mmol) of 2-bromopropene in 200 ml of THF is added in drops, so that the mixture boils easily. It is stirred for 15 more minutes and then cooled to 0° C. 396 mg (4 mmol) of copper(I) chloride is now added, stirred for another 15 minutes at 0° C. and ultimately 22.53 g (150 mmol) of (S)-carvone in 100 ml of THF is added. The reaction mixture is now heated slowly to room temperature and worked up analogously to the above cuprate addition, whereby 25.38 g (132 mmol) of title compound 1 is obtained as a colorless liquid.

(3S,5S)-3,5-Bis(1-methylethenyl)-2-methylcyclohexanol 2

1.14 g (30 mmol) of sodium borohydride is added in portions to a solution of 5.47 g (28.40 mmol) of 1 in 150 ml of absolute methanol at room temperature, and the reaction mixture is stirred for 4 more hours.

For working-up, it is hydrolyzed with water, extracted several times with dichloromethane and the combined organic phases are washed with saturated sodium chloride solution, dried on sodium sulfate, and the solvent is drawn off in a rotary evaporator. The residue is purified on a silica gel column (mobile solvent: EE:H=2:8; $R_f$=0.2).

4.55 g (23.43 mmol) of title compound 2 is obtained as a colorless liquid.

$^1$H-NMR (300 MHz, CDCl$_3$): δ=q 4.90 ppm [1]Hz (1H); m 4.85 ppm (2H); s 4.65 ppm (1H); ddd 4.00 [12.5+5+5]Hz (1H); s(br) 2.50 ppm (1H); m 2.2 ppm (2H); dm 1.95 ppm [12.5]Hz (1H); s 1.725 ppm (3H); s 1.70 ppm (3H); m 1.65 ppm (4H); d 0.75 ppm [7.5]Hz (3H)

MS (EI): m/z=194 (M$^+$)[5%]; 177 (M$^+$—OH)[47%]; 176 (M$^+$—H$_2$O) [48%]; 133 [80%]; 107 [81%]; 93 [45%]

Production of 2 by DIBAH reduction of 1

19.2 g (100 mmol) of 1 in 400 ml of toluene is introduced, and 100 ml (120 mmol) of DIBAH in toluene is added in drops at −78° C. It is heated slowly to room temperature, isopropanol/water is added and stirred for 30 more minutes. The precipitate is filtered off, and the filtrate is washed with sodium chloride solution, dried on sodium sulfate and concentrated by evaporation. The residue is chromatographed on silica gel (mobile solvent: EE:H=2:8), whereby 17.49 g (90.03 mmol) of title compound 2 accumulates as a colorless liquid.

(1S,5S)-1,5-Bis(1-methylethenyl)-2-methyl-3-(phenylmethoxy)cyclohexane 3

1.8 g (60 mmol) of an 80% sodium hydride suspension is added in portions to a solution of 4.50 g (23.16 mmol) of 2 in 60 ml of THF at room temperature, and it is stirred for 1 more hour. Then, 10.26 g (60 mmol) of benzyl bromide is added in drops at the given temperature. In addition, a spatula tip full of dimethylaminopyridine is added, and the reaction mixture is stirred overnight at room temperature.

For working-up, it is hydrolyzed with water and extracted with hexane. The combined organic phases are washed with saturated sodium chloride solution, dried on sodium sulfate, filtered, and the solvent is drawn off in a rotary evaporator. The residue is purified on a silica gel column (mobile solvent: hexane; $R_f$=0.9).

5.08 g (17.87 mmol) of title compound 3 is obtained as a colorless liquid.

$^1$H-NMR (300 MHz, CDCl$_3$): δ=m 7.35 ppm (5H); dd 4.875 [7.5+2.5]Hz (1H); s 4.75 ppm (1H); s 4.65 ppm (1H); dd 4.6 ppm [7.5+2.5]Hz (1H); s 4.55 ppm (2H); ddd 3.7 ppm [7.5+5+5]Hz (1; s(br) 2.55 ppm (1H); m 2.45 ppm (1H); m 2.15 ppm (1H); m 2.05 ppm (1H); m 1.75 ppm (9H); d 0.80 ppm [7.5]Hz (3H)

MS (EI): m/z=284 (M$^+$) [7%]; 282 [25%]; 193 (M$^+$—Bn) [7%]; 91 (Bn)[100%]

(1S,3S)-1,1'-4-methyl-5-(phenylmethoxy)-1,3-cyclohexanediyl]bis[ethanone]4

A weak ozone gas stream passes through a solution of 5.37 g (18.87 mmol) of 3 in 100 ml of absolute dichloromethane at −78° C. for about 30 minutes. After the reaction is completed (TLC monitoring), 10.5 g (40 mmol) of triphenylphosphine is added, and the reaction mixture is slowly heated to room temperature.

For working-up, it is diluted with dichloromethane, washed with water, the combined aqueous phases are re-extracted with dichloromethane and the combined organic phases are washed with saturated sodium chloride solution, dried on sodium sulfate, filtered off, and the solvent is drawn off in a rotary evaporator. The residue is purified on a silica gel column (mobile solvent: EE:H=8:2; $R_f$=0.1). 2.29 g (7.94 mmol) of title compound 4 is obtained as a colorless liquid.

$^1$H-NMR (300 MHz, CDCl$_3$): δ=m 7.3 ppm (5H); d 4.6 ppm [12]Hz (1H); d 4.5 ppm [12]Hz (1H); ddd 3.65 ppm [7.5+5+5]Hz (1H); m 2.85 ppm (1H); m 2.65 ppm (2H); s 2.12 ppm (3H); s 2.10 pm (3H); m 1.9–1.6 ppm (4H); d 0.85 ppm [7.5]Hz (3H)

MS (EI): m/z=288 (M$^+$)[1%]; 245 (M$^+$—CH$_3$CHO)[5%]; 197 (M$^+$—Bn)[4%]; 91 (Bn)[100%)]

IR(CHCl$_3$): ν=3034, 1706, 1357, 1262, 1095 cm$^{-1}$

(1S,5R)-1,5-Bis(acetyloxy)-2-methyl-3-(phenylmethoxy)cyclohexane 5

20.95 g (154 mmol) of potassium dihydrogen phosphate and 15.05 g (160 mmol) of urea/H$_2$O$_2$ adduct (Merck) are added to a solution of 2.28 g (7.9 mmol) of 4 in 160 ml of absolute dichloromethane at room temperature. Then, 8.40 g (40 mmol) of trifluoroacetic anhydride is slowly added in drops. It is stirred for 2 more hours at 40° C.

For working-up, it is quenched with saturated sodium bicarbonate, diluted with dichloromethane, the organic phase is washed once each with saturated sodium sulfite solution, water and saturated sodium chloride solution, dried on sodium sulfate, filtered off, and the solvent is drawn off in a rotary evaporator. Two products, which are separated on a silica gel column (mobile solvent: EE:H=4:6; F$_1$=1.32 g (4.11 mmol) R$_{f1}$=0.6 (diacetate); F$_2$=0.53 g (1.74 mmol) R$_{f2}$=0.5 (monoacetate), are obtained. The monoacetate was again subjected to the above procedure.

Spectroscopic data for 5:

$^1$H-NMR (300 MHz, CDCl$_3$): δ=m 7.35 ppm (5H); m 5.2 ppm (1H); m 5.1 ppm (1H); d 4.55 ppm [12]Hz (1H); d 4.5 ppm [12]Hz (1H); ddd 3.8 ppm [7.5+5+5]Hz (1H); m 2.6 ppm (1H); s 2.1 ppm (3H).; s 2.05 ppm (3H); m 1.85 ppm (4H); d 0.95 ppm [7.5]Hz (3H)

MS (EI): m/z=200 [3%]; 169 [5%]; 109 [25%]; 91 (Bn) [100%]

IR(CHCl$_3$): ν=1730, 1372, 1252, 1028 cm$^{-1}$

(1S,3S)-4-Methyl-5-(phenylmethoxy)-1,3-cyclohexanediol 6

378 mg (7 mmol) of sodium methanolate is added to a solution of 1.15 g (3.16 mmol) of 5 in 10 ml of absolute methanol at room temperature, and it is stirred for 24 hours at the given temperature.

For working-up, it is neutralized with saturated ammonium chloride solution and extracted with dichloromethane. The combined organic phases are washed with saturated sodium chloride solution, dried on sodium sulfate, filtered off, and the solvent is drawn off in a rotary evaporator. The residue is purified on a silica gel column (mobile solvent: EE; $R_f$=0.3).

558 mg (2.36 mmol) of title compound 6 is obtained as a crystalline substance.

$^1$H-NMR (300 MHz, CDCl$_3$): δ=m 7.35 ppm (5H); d 4.7 ppm [12]Hz (1H); d 4.4 ppm [12]Hz (1H); m 4.25 ppm (1H); m 3.9 ppm (1H); s(br) 3.8 ppm (1H); m 2.5 ppm (1H); m 2.3 ppm (2H); m 1.8–1.3 ppm (4H); d 1.2 ppm [7.5]Hz (3H)

MS (EI): m/z=218 (M$^+$—H$_2$O)[2%]; 107 [12%]; 91 (Bn) [100%]

(1S,5R)-1,5-Bis[[dimethyl(1,1-dimethylethyl)silyl]oxy]-2-methyl-3-(phenylmethoxy)-cyclohexane 7

557 mg (2.36 mmol) of 6 in 5 ml of absolute DMF is instilled in a solution of 1.51 g (10 mmol) of TBDMSCl and 1.36 g (20 mmol) of imidazole in 10 ml of absolute DMF at room temperature, and it is stirred overnight at the given temperature.

For working-up, it is diluted with hexane, hydrolyzed with water and shaken out with saturated ammonium chloride solution. The combined aqueous phases are re-extracted several times with hexane. The combined organic phases are washed with saturated sodium chloride solution, dried on sodium sulfate, filtered and the solvent is drawn off in a rotary evaporator. The residue is purified on a silica gel column (mobile solvent: hexane; $R_f$=0.9).

832 mg (1.79 mmol) of title compound 7 is obtained as a colorless liquid.

$^1$H-NMR (300 MHz, CDCl$_3$): δ=m 7.4 ppm (5H); d 4.6 ppm [12]Hz (1H); d 4.45 ppm [12]Hz (1H); m 4.1 ppm (2H); ddd 3.8 ppm [10+5+5]Hz; m 2.4 ppm (1H); m 1.7 ppm (1H); m 1.55 ppm (1H); d 0.95 ppm [7.5]Hz (3H); s 0.9 ppm (9H); s 0.85 ppm (9H); 4×s 0.75–0.5 ppm (12H)

MS (EI): m/z=449 (M$^+$—Me)[1%]; 407 [57%]; 318 [38%]; 199 [28%]; 157 [19%]; 91 [100%]

(3S,5R)-3,5-Bis[[dimethyl(1,1-dimethylethyl)silyl]oxy]-2-methylcyclohexanol 8

A spatula tip full of 10% Pd/C is added to a solution of 1.14 g (2.45 mmol) of 7 in 60 ml of absolute ethanol. The reaction flask is equipped with a hydrogen balloon, and it is stirred overnight.

For working-up, it is filtered off, and the filter cake is flushed thoroughly with ethanol. Finally, the solvent is concentrated by evaporation in a rotary evaporator, and the residue is purified on a silica gel column (mobile solvent: EE:H=3:7; $R_f$=0.6). 735 mg (1.96 mmol) of title compound 8 is obtained as a colorless liquid.

$^1$H-NMR (300 MHz, CDCl$_3$): δ=tt 4.3 ppm [12+4]Hz (1H); m 4.02 ppm (1H); d(br) 3.82 ppm [9]Hz (1H); m 2.32 (1H); m 2.05 ppm (1H); m 1.48 ppm (1H); d 1.10 ppm [7.5]Hz (3H); s 0.9 ppm (9H); s 0.88 ppm (9H); 4×s 0.75–0.5 ppm (12H)

MS (EI): m/z=317 (M$^+$—Bu)[7%]; 241 (M$^+$—tBDMSiOH)[8%]; 227 [30%]; 199 [75%]; 185 [81%]; 159 [50%]; 157 [47%]; 115 [30%]; 75 [99%]; 73 [100%]

(3S,5S)-3,5-Bis[[dimethyl(1,1-dimethylethyl)silyl]oxy]-2-methylcyclohexanone 9

547 mg (7 mmol) of DMSO is slowly added in drops to a solution of 444 mg (3.5 mmol) oxalyl chloride in 20 ml of absolute dichloromethane at −78° C. It is stirred for 20 more minutes at the given temperature. Then, 592 mg (1.58 mmol) of 8 in 5 ml of absolute dichloromethane is added, and it is stirred again for 15 more minutes. Then, 2.83 g of triethylamine is added, and the reaction mixture is slowly heated to room temperature.

For working-up, dichloromethane is added and acidified with dilute HCl. The aqueous phase is re-extracted another two times with dichloromethane, the combined organic phases are washed with saturated sodium chloride solution, dried on sodium sulfate, filtered off, and the solvent is drawn off in a rotary evaporator. The residue is chromatographed on a silica gel column (mobile solvent: EE:H=2:8; $R_f$=0.4).

550 mg (1.48 mmol) of title compound 9 is obtained as a white, crystalline substance.

$^1$H-NMR (300 MHz, CDCl$_3$): δ=m 4.3 ppm (1H); m 4.15 ppm (1H); ddd 2.7 ppm [15+5+2]Hz (1H); m 2.4 ppm (2H); m 2.2 ppm (1H); m 1.8 ppm (1H); d 1.05 ppm [7.5]Hz (3H); s 0.9 ppm (9H); s 0.85 ppm (9H); s 0.5 ppm (12H)

MS (EI): m/z=315 (M⁺—Bu)[27%]; 199 [5%]; 157 [100%]; 133 [8%]; 115 [13%]; 75 [16%]; 73 [22%]

IR(CHCl$_3$): ν=2957, 2931, 2886, 2858, 1713, 1472, 1257, 1097, 1004, 838 cm$^{-1}$

(3S,5s)-3,5-Bis[[dimethyl(1,1-dimethylethyl)silyl]oxy]-1-ethinyl-2-methylcyclohexanol 10

At 0° C., acetylene is introduced into 50 ml of THF for 20 minutes. 1.25 ml n-Butyllithium solution (1.6M in hexane, 2 mmol) is added in drops and stirred for 20 more minutes at this temperature. Then, 215 mg (0.58 mmol) of 9 in 2 ml of THF is added in drops and stirred for 2 hours. Then, it is quenched with saturated ammonium chloride solution, diluted with ethyl acetate, and the organic phase is washed with saturated sodium chloride solution, dried on sodium sulfate and the solvent is removed. The residue is purified on silica gel by column chromatography (mobile solvent: EE:H=4:6, R$_f$=0.6), whereby 163 mg (0.41 mmol) of title compound 10 is obtained as a white crystalline substance.

$^1$H-NMR (300 MHz, CDCl$_3$): δ=m 4.22 ppm (1H); m 4.06 ppm (1H); ddd 2.48 ppm [15+4+2]Hz (1H); dbr 2.09 ppm (1H); m 1.69 ppm (2H); m 1.58 ppm (1H); d 1.25 ppm [7.5]Hz (3H); s 0.92 ppm (9H); s 0.89 ppm (9H); s 0.1 ppm (12H)

(3S,5R)-3,5-Bis[[dimethyl(1,1-dimethylethyl)silyl]oxy]-1-ethinyl-2-methyl-1-cyclohexene 11

90 mg (0.23 mmol) of 10 in 8 ml of pyridine is introduced, and 50 μl of thionyl chloride is added under argon. It is stirred for 10 minutes at room temperature, poured onto ice water and extracted with ethyl acetate. The organic phase is washed with sodium bicarbonate solution and sodium chloride solution, dried on sodium sulfate, the solvent is removed and the crude product is purified by chromatography on silica gel (mobile solvent: EE:H=1:19; R$_f$=0.9), whereby 71 mg (0.20 mmol) of title compound 11 is obtained as a colorless oil.

$^1$H-NMR (300 MHz, CDCl$_3$): δ=m 4.21 ppm (1H); m 4.09 ppm (1H); s 3.06 (1H); sbr 1.93 ppm (3H); s 0.91 ppm (9H); s 0.89 ppm (9H); s 0.6 ppm (12H)

IR (KBr): ν=3310, 2085, 1260, 835 cm$^{-1}$

MS (EI): m/z=380 (M⁺)[3%]; 365 (M⁺—Me)[25%]; 323 [80%]; 248 [100%]

(3S,5R)-3,5-Bis(acetyloxy)-2-methylcyclohexanol 12

A spatula tip full of 10% Pd/C is added to a solution of 60 mg (0.19 mmol) of 5 in 10 ml of absolute ethanol. The reaction flask is equipped with a hydrogen balloon, and it is stirred overnight.

For working-up, it is filtered off, and the filter cake is flushed thoroughly with ethanol. Ultimately, the solvent is concentrated by evaporation in a rotary evaporator, and the residue is purified on a silica gel column (mobile solvent: EE:H=1:1; R$_f$=0.3). 44 mg (0.19 mmol) of title compound 12 is obtained as a colorless oil.

$^1$H-NMR (300 MHz, CDCl$_3$): δ=m 5.2 ppm (2H); s (br) 4.0 ppm (1H); s 2.1 ppm (3H); m 2.05 ppm (3H); s 2.025 ppm (3H); m 1.65 ppm (3H); d 1.00 ppm [7.5]Hz (3H)

(3S,5S)-3,5-Bis(acetyloxy)-2-methylcyclohexanone 13

25 mg of ruthenium dioxide is added to a solution of 50 mg (0.22 mmol) of 12 in 1 ml of tetrachloromethane at room temperature. The suspension is mixed with 0.85 ml of a 0.28 molar sodium metaperiodate solution (0.24 mmol) in water. After 2 hours of stirring at the given temperature, another 0.5 ml of the aqueous sodium metaperiodate solution (0.14 mmol) is added, and it is again stirred for 2 hours.

For working-up, the catalyst is filtered off, the suspension is diluted with ethyl acetate, and the filter cake is thoroughly rewashed with ethyl acetate. The combined organic phases are washed with saturated sodium chloride solution, dried on sodium sulfate, filtered, and the solvent is drawn off in a rotary evaporator.

73.4 mg of title compound 13 is obtained as a colorless oil.

$^1$H-NMR (300 MHz, CDCl$_3$): δ=m 5.4 ppm (1H); m 5.2 ppm (1H); ddd 2.9 ppm [15+5+2.5]Hz (1H); m 2.6 ppm (1H); m 2.45 ppm (2H); m 2.05 ppm (1H); s 2.05 ppm (6H); d 1.05 ppm [7.5]Hz (3H)

(1S,5S)-1,5-Bis(1-methylethenyl)-3-[[(1,1-dimethylethyl)diphenylsilyl]oxy]-2-methylcyclohexane 14

7.67 g (39.6 mmol) of 2 in 50 ml of DMF is introduced, and 6.54 g (96 mmol) of imidazole and 12.5 ml (48 mmol) of tert-butyldiphenylsilyl chloride in 80 ml of DMF are added. It is stirred overnight at room temperature, and then quenched with sodium chloride solution, extracted with ethyl acetate, the organic phase is washed with sodium chloride solution and dried on sodium sulfate. After the concentration by evaporation, the residue is chromatographed on silica gel (mobile solvent: EE:H=2:8), whereby 17.05 g (39.4 mmol) of title compound 14 accumulates as a colorless liquid.

$^1$H-NMR (300 MHz, CDCl$_3$): δ=m 7.70 ppm (4H); m 7.39 ppm (6H); s 4.78 ppm (1H); s 4.60 ppm (1H); s 4.52 ppm (1H); s 4.13 ppm (1H); m 3.95 ppm (1H); m 2.33 ppm (1H); m 2.08 ppm (1H); m 1.2 ppm (1H); m 1.75 ppm (2H); m 1.59 ppm (2H); s 1.59 ppm (3H); s 1.42 ppm (3H); s 1.09 ppm (9H); d 0.81 ppm [7]Hz (3H)

(1S,3S)-1,1'-[5-[[(1,1-Dimethylethyl)diphenylsilyl]oxy]-4-methyl-1,3-cyclohexanediyl]bis[ethanone]15

25.75 g (59.5 mmol) of 14 in 420 ml of dichloromethane and 140 ml of methanol are dissolved, and ozone/oxygen mixture (ozone generator) is introduced at −78° C. until the solution is colored light blue. Excess ozone is expelled with nitrogen and then mixed with 9.32 g (150 mmol) of dimethyl sulfide. It is heated to room temperature, the mixture is concentrated by evaporation and the residue is chromatographed on silica gel (mobile solvent EE:H=6:4), whereby 41.1 g (55.19 mmol) of title compound 15 is obtained as a colorless liquid.

$^1$H-NMR (300 MHz, CDCl$_3$): δ=m 7.69 ppm (4H); m 7.40 ppm (6H); m 3.82 ppm (1H); m 2.64 ppm (1H); dt 2.58 ppm [12+4]Hz (1H); m 2.27 ppm (1H); s 1.98 ppm (3H); m 1.78 ppm (3H); s 1.70 ppm (3H); 1.61 ppm (1H); s 1.09 ppm (9H), d 0.83 ppm [7]Hz (3H)

(1S,5S)-1,5-Bis(acetyloxy)-3-[[(1,1-dimethylethyl)-diphenylsilyl]oxy]-2-methylcyclohexane 16

Analogously to Example 5, 17.68 g (40.5 mmol) of 15 is reacted, whereby 16.99 g (36.25 mmol) of title compound 16 accumulates as a colorless oil.

$^1$H-NMR (300 MHz, CDCl$_3$): δ=m 7.68 ppm (4H); m 7.38 ppm (6H); m 5.05 ppm (1H); m 4.99 ppm (1H); m 3.98 ppm (1H); m 2.37 ppm (1H); s 2.08 ppm (3H); s 1.80 ppm (3H); m 1.70 ppm (3H); 1.58 ppm (1H); s 1.09 ppm (9H); d 1.02 ppm [7]Hz (3H)

(1S,3S)-5-[[(1,1-Dimethylethyl)diphenylsilyl]oxy]-4-methyl-1,3-cyclohexanediol 17

469 mg (1 mmol) of 16 is dissolved in 10 ml of THF and mixed at 0° C. with 3.4 ml of methylmagnesium bromide solution (3M in THF). After 3 hours at this temperature, it is hydrolyzed with ammonium chloride solution, extracted with ethyl acetate and dried on sodium sulfate. The solvent is removed, and the residue is purified on silica gel (mobile solvent: EE:H=8.2), whereby 231 mg (0.6 mmol) of title compound 17 is obtained.

$^1$H-NMR (300 MHz, CDCl$_3$): δ=m 7.69 ppm (4H); m 7.42 ppm (6H); m 4.41 ppm (1H); m 4.09 ppm (1H); m 3.89 ppm (1H); m 2.32 ppm (1H); m 2.00 ppm (1H); m 1.58 ppm (1H); m 1.42 ppm (1H); 1.28 ppm (1H); s 1.09 ppm (9H); d 1.09 ppm [7]Hz (3H)

(1S,5S)-1,5-Bis(1-ethoxyethoxy)-3-[[(1,1-dimethylethyl)diphenylsilyl]oxy]-2-methylcyclohexane 18

5.11 g (13.3 mmol) of 17 is stirred with 2.96 g of (41 mmol) of ethyl vinyl ether and 327 mg (1.3 mmol) of pyridinium-p-toluene sulfonate in 80 ml of dichloromethane at room temperature for 3 hours. Then, it is washed with sodium chloride solution, dried on sodium sulfate and concentrated by evaporation. The residue is chromatographed on silica gel (mobile solvent: EE:H=1:1), whereby 6.48 g (12.14 mmol) of title compound 18 accumulates.

(3S,5R)-3,5-Bis(1-ethoxyethoxy)-2-methylcyclohexanol 19

6.48 g (12.14 mmol) of 18 and 6.31 g (20 mmol) of tetrabutylammonium fluoride (hydrate) in 150 ml of THF is stirred overnight at room temperature. Then, it is hydrolyzed with sodium chloride solution, extracted with ethyl acetate, washed with sodium chloride solution and dried on sodium sulfate. After concentration by evaporation, the residue is chromatographed on silica gel (mobile solvent: EE:H=8:2), whereby 2.41 g (8.3 mmol) of title compound 19 is obtained.

$^1$H-NMR (300 MHz, CDCl$_3$): δ=m 4.78 ppm (2H); m 4.12 ppm (2H); m 3.89 ppm (1H); m 3.68 ppm (2H); m 3.49 ppm (2H); m 2.30 ppm (1H); m 1.70 ppm (1H); m 1.43 ppm (3H); d 1.34 ppm [7]Hz (6H); t 1.21 ppm [7]Hz (6H); d 1.09 ppm [7]Hz (3H)

(3S,5S)-3,5-Bis(1-ethoxyethoxy)-2-methylcyclohexanone 20

Analogously to Example 9, 2.4 g (8.3 mmol) of 19 is reacted, whereby 2.17 g (7.5 mmol) of title compound 20 accumulates as a colorless oil.

$^1$H-NMR (300 MHz, CDCl$_3$): δ=m 4.74 ppm (2H); m 4.18 ppm (2H); m 3.60 ppm (2H); m 3.48 ppm (2H); m 2.81 ppm (1H); m 2.42 ppm (3H); m 1.83 ppm (1H); d 1.38 ppm [7]Hz (6H); t 1.20 ppm [7]Hz (6H); d 1.09 ppm [7]Hz (3H)

(3S,5)-3,5-Bis(1-ethoxyethoxy)-1-ethinyl-2-methylcyclohexanol 21

2.00 g (6.94 mmol) of 20 ia reacted analogously to Example 10, and 1.87 g (5.96 mmol) of title compound 21 is obtained as a colorless oil.

(3S,5S)-3,5-Bis(1-ethoxyethoxy)-1-ethinyl-2-methyl-1-cyclohexene 22

Analogously to Example 11, 1.87 g (5.96 mmol) of 21 is reacted, and 1.39 g (4.67 mmol) of title compound 22 is obtained as a yellowish oil.

$^1$H-NMR (300 MHz, CDCl$_3$): m 4.80 ppm (2H); m 4.00 ppm (2H); m 3.63 ppm (2H); m 3.49 ppm (2H); d 3.09 ppm [4]Hz (1H); m 2.54 ppm (1H); m 2.14 ppm (3H); s 2.00 ppm (3H); s 1.95 ppm (3H); d 1.38 ppm [7]Hz (6H); t 1.20 ppm [7]Hz (6H)

Reaction Diagram 1

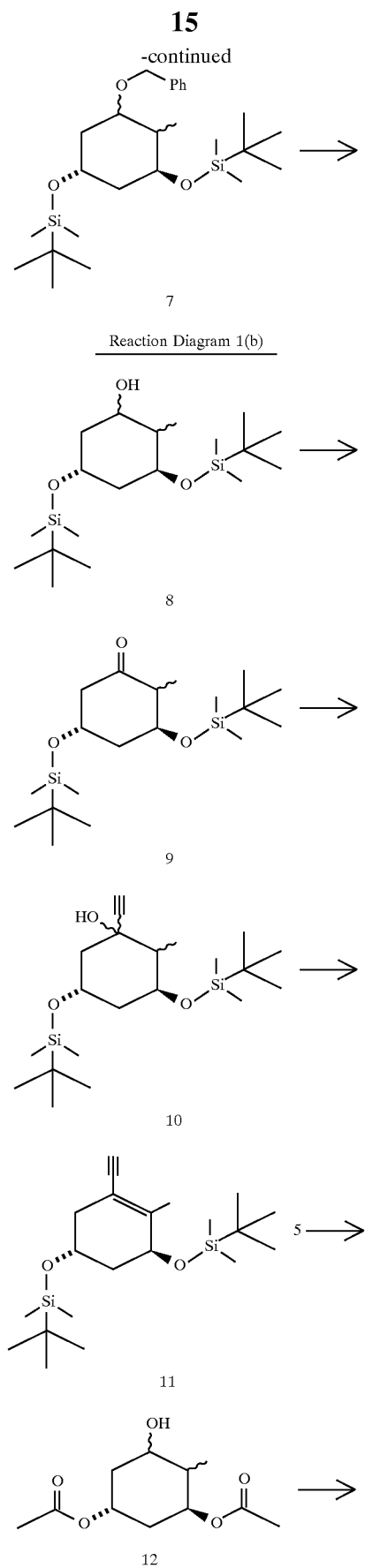

-continued

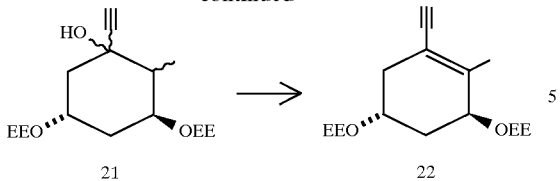

We claim:
1. A cyclohexanone compound of formula I,

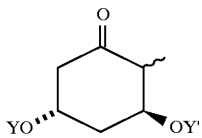

in which Y and Y' each mean a hydrogen atom, an alkanoyl group with 1 to 9 carbon atoms, an aroyl group, an alkyl-substituted or aryl-substituted or mixed aryl-alkyl-substituted silyl or silylalkoxyalkyl group, an alkoxyalkyl group, a tetrahydrofuranyl group or a tetrahydropyranyl group.

2. A cyclohexanone compound according to claim 1, in which Y and Y' mean acetyl, propionyl, pivaloyl or benzoyl or trimethylsilyl (TMS), triethylsilyl (TES), tert-butyldimethylsilyl (TBDMS), tert-butyldiphenylsilyl (TBDPS) or triisopropylsilyl (TIPS) or methoxymethyl (MOM), methoxyethoxymethyl (MEM), ethoxyethyl (EE), trimethylsilylethoxymethyl (SEM), tetrahydrofuranyl (THF) or tetrahydropyranyl (THP) and can be the same or different.

3. A cyclohexanone compound according to claim 1, namely (3S,5S)-3,5-Bis[[dimethyl(1,1-dimethylethyl)silyl]oxy]-2-methylcyclohexanone,
(3S,5S)-3,5-bis[[(1,1-dimethylethyl)diphenylsilyl]oxy]-2-methylcyclohexanone,
(3S,5S)-3,5-bis[(triethylsilyl)oxy]-2-methylcyclohexanone,
(3S,5S)-3,5-bis(acetoxy)-2-methylcyclohexanone,
(3S,5S)-3,5-bis(2,2-dimethyl-1-oxopropoxy)-2-methylcyclohexanone,
(3S,5S)-3,5-bis(benzoyloxy)-2-methylcyclohexanone,
(3S,5S)-3,5-bis(1-ethoxyethoxy)-2-methylcyclohexanone.

4. A process for the production of a cyclohexanone compound of formula I according to claim 1, by reaction of (S)-carvone with a copper-containing organometallic compound to compound VIII,

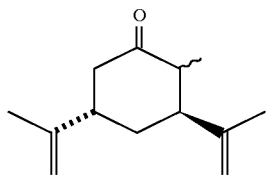

reaction of compound VIII to the compound of general formula IX

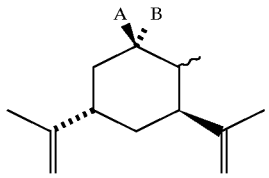

subsequent oxidative cleavage of the vinyl group to the corresponding methyl ketones of general formula X,

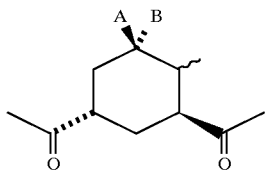

conversion of the compounds of general formula X by Baeyer-Villiger oxidation to the diacetate of general formula XI

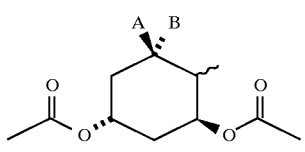

saponification of the acetate groups and conversion to compounds of general formula XII,

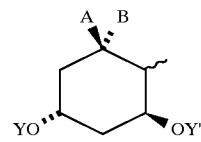

in which Y and Y' have the meanings mentioned in claims 1 and 2, and in general formulas IX, X, XI and XII, A and B together mean a free or protected carbonyl group, whereby the protective groups are selected from dialkoxyketal, 1,3-dioxane, 1,3-dioxolane, dialkylhydrazone, tosylhydrazone, oxime, alkyl- or benzyloxime ether or A or B means a hydrogen atom and the corresponding other group B or A means a hydroxy group, which can be free or protected, whereby the protective groups are selected from benzyl ether, p-methoxybenzyl ether, o-, m-, p-nitrobenzyl ether, TBDMS ether, TIPS ether, TBDPS ether, TES ether, MOM ether, MEM ether, SEM ether, EE ether, THP ether and THF ether, and subsequent cleavage of the ketal or hydrazone group or selective cleavage of alcohol protective group A or B and oxidation.

5. A compounds of the formula IX

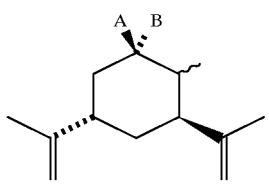

in which A and B together mean a protected carbonyl group, whereby the protective groups are selected from dialkoxyketal, 1,3-dioxane, 1,3-dioxolane, dialkylhydrazone, tosylhydrazone, oxime, alkyl- or benzyloxime ether or A or B means a hydrogen atom and the corresponding other group B or A means a hydroxy group, which can be free or protected, whereby the protective groups are selected from benzyl ether, p-methoxybenzyl ether, o-, m-, p-nitrobenzyl ether, TBDMS ether, TIPS ether, TBDPS ether, TES ether, MOM ether, MEM ether, SEM ether, EE ether, THP ether and THF ether.

6. A compound of claim 5, which is:
(1S,5S)-1,5-Bis(1-methylethenyl)-2-methyl-3-(phenylmethoxy)cyclohexane,
(E)-(3S,5S)-3,5-bis(1-methylethenyl)-2-methylcyclohexanone oxime,
(Z)-(3S,5S)-3,5-bis(1-methylethenyl)-2-methylcyclohexanone oxime,
(E)-(3S,5S)-3,5-bis(1-methylethenyl)-2-methylcyclohexanone-O-methyloxime,
(Z)-(3S,5S)-3,5-bis(1-methylethenyl)-2-methylcyclohexanone-O-methyloxime or
(1S,5S)-1,5-bis(1-methylethenyl)-3-[[(1,1-dimethylethyl)diphenylsilyl]oxy]-2-methylcyclohexane.

7. A compound of the formula X

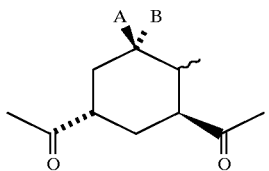

in which A and B together mean a free or protected carbonyl group, whereby the protective groups are selected from dialkoxyketal, 1,3-dioxane, 1,3-dioxolane, dialkylhydrazone, tosylhydrazone, oxime, alkyl- or benzyloxime ether or A or B means a hydrogen atom and the corresponding other group B or A means a hydroxy group, which can be free or protected, whereby the protective groups are selected from benzyl ether, p-methoxybenzyl ether, o-, m-, p-nitrobenzyl ether, TBDMS ether, TIPS ether, TBDPS ether, TES ether, MOM ether, MEM ether, SEM ether, EE ether, THP ether and THF ether.

8. A compound of claim 7, which is:
(1S,3S)-1,1'-[4-Methyl-5-(phenylmethoxy)-1,3-cyclohexanediyl]bis[ethanone],
(E)-(1S,3S)-1,1'-[5-(hydroxyimino)-4-methyl-1,3-cyclohexanediyl]bis[ethanone],
(Z)-(1S,3S)-1,1'-[5-(hydroxyimino)-4-methyl-1,3-cyclohexanediyl]bis[ethanone],
(E)-(1S,3S)-1,1'-[5-(methoxyimino)-4-methyl-1,3-cyclohexanediyl]bis[ethanone],
(Z)-(1S,3S)-1,1'-[5-(methoxyimino)-4-methyl-1,3-cyclohexanediyl]bis[ethanone] or
(1S,3S)-1,1'-[5-[[(1,1-dimethylethyl)diphenylsilyl]oxy]-4-methyl-1,3-cyclohexanediyl]bis[ethanone].

9. A compound of the formula XI,

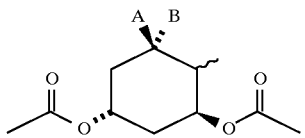

in which A and B together mean a free or protected carbonyl group, whereby the protective groups are selected from dialkoxyketal, 1,3-dioxane, 1,3-dioxolane, dialkylhydrazone, tosylhydrazone, oxime, alkyl- or benzyloxime ether or A or B means a hydrogen atom and the corresponding other group B or A means a hydroxy group, which can be free or protected, whereby the protective groups are selected from benzyl ether, p-methoxybenzyl ether, o-, m-, p-nitrobenzyl ether, TBDMS ether, TIPS ether, TBDPS ether, TES ether, MOM ether, MEM ether, SEM ether, EE ether, THP ether and THF ether.

10. A compound of claim 9, which is:
(1S,5R)-1,5-Bis(acetyloxy)-2-methyl-3-(phenylmethoxy)cyclohexane,
(3S,5R)-3,5-bis(acetyloxy)-2-methylcyclohexanol,
(E)-(3S,5R)-3,5-bis(acetyloxy)-2-methylcyclohexanone oxime,
(Z)-(3S,5R)-3,5-bis(acetyloxy)-2-methylcyclohexanone oxime,
(E)-(3S,5R)-3,5-bis(acetyloxy)-2-methylcyclohexanone-O-methyloxime,
(Z)-(3S,5R)-3,5-bis(acetyloxy)-2-methylcyclohexanone-O-methyloxime or
(1S,5S)-1,5-bis(acetyloxy)-3-[[(1,1-dimethylethyl)diphenylsilyl]oxy]-2-methylcyclohexane.

11. A compound of the formula XII,

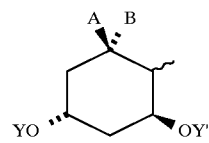

in which Y and Y' each mean a hydrogen atom, an alkanoyl group with 1 to 9 carbon atoms, an aroyl group, an alkyl-substituted or aryl-substituted or mixed aryl-alkyl-substituted silyl or silylalkoxyalkyl group, alkoxyalkyl group, a tetrahydrofuranyl group or a tetrahydropyranyl group, and A and B together mean a free or protected carbonyl group, whereby the protective groups are selected from dialkoxyketal, 1,3-dioxane, 1,3-dioxolane, dialkylhydrazone, tosylhydrazone, oxime, alkyl- or benzyloxime ether or A or B means a hydrogen atom and the corresponding other group B or A means a hydroxy group, which can be free or protected, whereby the protective groups are selected from benzyl ether, p-methoxybenzyl ether, o-, m-, p-nitrobenzyl ether, TBDMS ether, TIPS ether, TBDPS ether, TES ether, MOM ether, MEM ether, SEM ether, EE ether, THP ether and THF ether.

12. A compound of claim 11, which is:
(1S,3S)-4-Methyl-5-(phenylmethoxy)-1,3-cyclohexanediol,
(1S,5R)-1,5-bis[[dimethyl(1,1-dimethylethyl)silyl]oxy]-2-methyl-3-(phenylmethoxy)cyclohexane,
(3S,5R)-3,5-bis[[dimethyl(1,1-dimethylethyl)silyl]oxy]-2-methylcyclohexanol,
(3S,5R)-3,5-bis(acetyloxy)-2-methylcyclohexanol,
(E)-(3S,5R)-3,5-dihydroxy-2-methylcyclohexanone oxime,
(Z)-(3S,5R)-3,5-dihydroxy-2-methylcyclohexanone oxime,
(E)-(3S,5R)-3,5-dihydroxy-2-methylcyclohexanone-O-methyloxime,
(Z)-(3S,5R)-3,5-dihydroxy-2-methylcyclohexanone-O-methyloxime,
(E)-(3S,5R)-3,5-bis[[dimethyl(1,1-dimethylethyl)silyl]oxy]-2-methylcyclohexanone oxime,
(Z)-(3S,5R)-3,5-bis[[dimethyl(1,1-dimethylethyl)silyl]oxy]-2-methylcyclohexanone oxime,
(E)-(3S,5R)-3,5-bis[[dimethyl(1,1-dimethylethyl)silyl]oxy]-2-methylcyclohexanone-O-methyloxime,
(Z)-(3S,5R)-3,5-bis[[dimethyl(1,1-dimethylethyl)silyl]oxy]-2-methylcyclohexanone-O-methyloxime,
(1S,5S)-1,5-bis(acetyloxy)-3-[[dimethyl(1,1-dimethylethyl)diphenylsilyl]oxy]-2-methylcyclohexane,
(1S,3S)-5-[[(1,1-dimethylethyl)diphenylsilyl]oxy]-4-methyl-1,3-cyclohexanediol,
(1S,5S)-1,5-bis(1-ethoxyethoxy)-3-[[(1,1-dimethylethyl)-diphenylsilyl]oxy]-2-methylcyclohexane or
(3S,5R)-3,5-bis(1-ethoxyethoxy)-2-methylcyclohexanol.

* * * * *